United States Patent [19]

Kim

[11] 4,165,440

[45] Aug. 21, 1979

[54] CATALYTIC HYDRATION OF ETHYLENE OXIDE TO ETHYLENE GLYCOL

[75] Inventor: Leo Kim, Houston, Tex.

[73] Assignee: Shell Oil Company, Houston, Tex.

[21] Appl. No.: 838,526

[22] Filed: Oct. 3, 1977

Related U.S. Application Data

[63] Continuation-in-part of Ser. No. 730,049, Oct. 6, 1976, abandoned.

[51] Int. Cl.$^2$ .............................................. C07C 29/00
[52] U.S. Cl. ................................................... 568/867
[58] Field of Search ....................... 260/635 E, 2.2 R; 568/867

[56] References Cited

U.S. PATENT DOCUMENTS

| | | | |
|---|---|---|---|
| 3,028,434 | 4/1962 | Weisz | 260/635 E |
| 3,041,317 | 6/1962 | Gibbs et al. | 260/2.2 R |
| 3,091,647 | 5/1963 | Hamilton et al. | 260/635 E |
| 3,985,501 | 10/1976 | Grot | 260/2.2 R |

*Primary Examiner*—James H. Reamer
*Attorney, Agent, or Firm*—Howard W. Haworth; Ronald L. Clendenen

[57] ABSTRACT

An improved process for the low temperature preparation of ethylene glycol by the catalytic hydration of ethylene oxide using a fluorinated alkyl sulfonic acid ion exchange resin is described.

4 Claims, No Drawings

CATALYTIC HYDRATION OF ETHYLENE OXIDE TO ETHYLENE GLYCOL

This application is a continuation-in-part of copending application Ser. No. 730,049, filed Oct. 6, 1976 now abandoned.

BACKGROUND OF THE INVENTION

1. Field of the Invention

This invention relates to a process for the preparation of ethylene glycol by the acid catalyzed hydration of ethylene oxide utilizing a fluorinated alkyl sulfonic acid ion exchange resin catalyst.

2. Description of the Prior Art

The production of ethylene glycol by thermal and acid catalyzed hydration of ethylene oxide is a well known reaction. A large number of acids have been used including acid ion exchange resins. U.S. Pat. No. 3,091,647 issued May 28, 1963 to Hamilton et al and U.S. Pat. No. 3,028,434 issued Apr. 3, 1962 to Weisz both teach the hydration of ethylene oxide using conventional acid ion exchange resins, but they do not teach that the use of fluorinated alkyl sulfonic acid ion exchange resins provides enhanced results at low temperatures. U.S. Pat. No. 3,985,501 issued Oct. 12, 1976 to Grot, U.S. Pat. No. 3,041,317 issued June 26, 1962 to Gibbs et al and U.S. Pat. No. 3,282,875 issued Nov. 1, 1966 to Connolly et al teach that fluorinated resins are more stable at elevated temperatures than conventional resins but they do not teach that the fluorinated resins would have superior properties at the lower temperatures where the conventional resins would be equally stable.

SUMMARY OF THE INVENTION

The present invention is a process for producing ethylene glycol from ethylene oxide at relatively low temperatures using a type of acid ion exchange resin which gives higher reaction rates and higher selectivity than conventional acid ion exchange resins.

The process for the preparation of ethylene glycol comprises contacting an ethylene oxide/water mixture with an acid ion exchange resin containing fluorinated alkyl sulfonic acid groups at a temperature in the range of about 20° C. to about 115° C., fractionally distilling the resulting liquid mixture to separate the ethylene glycol from the unreacted starting materials and any polymerization products.

DESCRIPTION OF THE PREFERRED EMBODIMENTS

The invention relates to a process for the preparation of ethylene glycol by the addition of water to ethylene oxide catalyzed by an acid ion exchange resin containing fluoroalkyl sulfonic acid groups.

The process involves contacting an ethylene oxide/water solution with the fluoroalkyl sulfonic acid ion exchange resin either by a batch slurry procedure or by passing the solution of ethylene oxide and water over a bed or column of ion exchange resin. The preferred method is the use of a fixed bed of ion exchange resin and passing the solution of ethylene oxide and water through or over the bed.

The temperature at which the ethylene oxide/water solution is contacted with the ion exchange resin is in the range of from about 20° C. to about 115° C., preferably from about 50° C. to about 110° C. and more preferably from about 75° C. to about 105° C.

The initial weight ratio of water to ethylene oxide in the solution contacting the catalyst is between about 1:1 and 100:1, preferably between about 1.5:1 to 20:1 and most preferably between about 3:1 to about 15:1.

The fluoroalkyl sulfonic acid resins are those having the group CFSO$_3$H as an acidic moeity of the resin, and a Pka of less than about 2.5. The preferred fluorinated alkyl sulfonic acid resins are those having the formula:

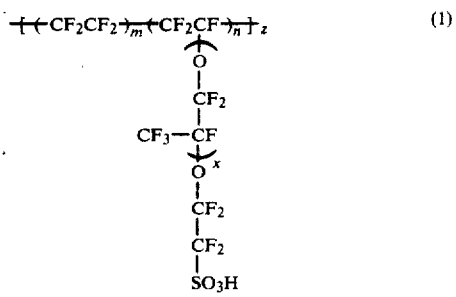

When n is at least one and the sum of m, n, x and z are such that the equivalent weight is 2000 or less, preferably between about 900 and about 2000, and most preferably between about 960 and about 1200. These resins are further described in U.S. Pat. No. 3,282,875, filed November 1, 1966, which is incorporated herein.

The fluoroalkyl sulfonic acid resins can also have the formulas:

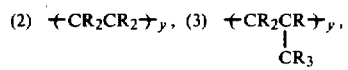

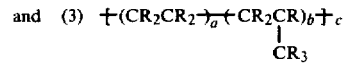

where R is individually a hydrogen, a fluorine and a —SO$_3$H group and where at least some of the carbons attached to greater than one R simultaneously have one R, a —SO$_3$H and one a fluorine and where y and the sum of a, b and c and R are such that the equivalent weight is less than about 2000, preferably between about 300 and about 1500.

The resin may be used neat or it may be deposited on a support. Preferred supports are those which have surface areas between about 10 square meters (m$^2$/gram) to about 200 m$^2$/gram, most preferably between about 30 m$^2$/gram and about 120 m$^2$/gram. The preferred pore diameter is between about 10 angstroms (Å) and about 800 Å, preferably between about 50 Å and about 500 Å. Preferred supports are silicon dioxide, aluminas, porous glass beads and clay. The most preferred support is silicon dioxide. The amount of resin used per amount of support is in the range of about ½ weight percent to about 12 weight percent, preferably about 6 weight percent to about 10 weight percent based on total weight.

The fluoralkyl sulfonic acid ion exchange resins of this invention may be made by known methods of organic chemistry and certain of the resins are commercially available. The resins of formula 1 are made by the following series of reactions:

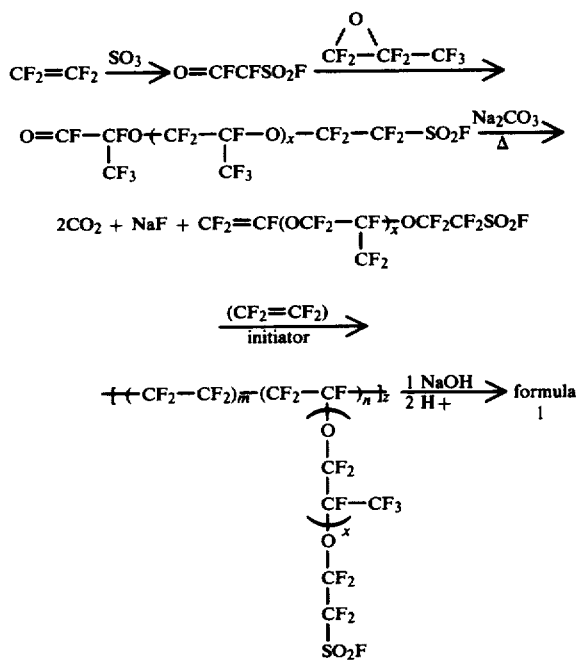

The resins of formula 2-4 are prepared by starting with the hydrocarbon polymer, i.e. polyethylene, polypropylene and their copolymers, sulfonating the polymer to the desired extent, then fluorinating the sulfonated polymer.

The ethylene oxide/water solution does not normally require an additional solvent but if desired, inert solvents such as ethers, e.g. di- and tri-ethylene glycol may be employed. The preferred weight percent ratio of solvent to ethylene oxide is between about 1.0% to about 50%, most preferably between about 5% and about 30%.

The rate at which the solution is passed over the catalyst is somewhat dependent on the concentration of ethylene oxide, the density of $CF_2SO_3H$ groups and the temperature of hydration. The hydration is exothermic and therefore some care must be taken. LHSV's of between about 0.01 hour$^{-1}$ and about 5 hours$^{-1}$ are preferred and between about 0.1 hour$^{-1}$ and about 1 hour$^{-1}$ are most preferred when using the concentrations, resin/dispersant ratio, and temperatures employed in this invention.

The ethylene glycol prepared by the process of this invention is useful as coolant in motors, as antifreeze, and as fluid in hydraulic systems.

The following Illustrative Embodiments are set forth for illustrative purposes and are not to be taken as limiting the scope of this invention in any way.

ILLUSTRATIVE EMBODIMENT I

Davison silica 952 (300 m$^2$/g surface area, 1.65 ml/g pore volume, 210 Å average pore diameter) was dried in the vacuum oven overnight at 100° C. and 2 mm. Calcination was at 510° C. for 2 hours.

In the dry box, to 32 g of calcined silica contained in a roundbottomed flask was added dropwise 46 ml of 5.5% solution of Nafion XR (Formula 1 resin) (2.05 g of Nafion) in ethanol (supplied by DuPont Chemical Co., 2897-30). The mixture was vigorously stirred with a mechanical stirrer during the addition. Stirring was continued for 30 minutes after the addition was complete. Ethanol was removed from the solid on the rotary evaporator in the dry box at 25° C. and 1 mm pressure for 2 hours and at 60° C. and 1 mm pressure for 4 hours. The product was ground up so that it passed through a number 60 sieve.

ILLUSTRATIVE EMBODIMENT II (a) A solution having a water to ethylene oxide (EO) weight ratio of 10:1 was passed over a bed having approximately 6 percent by weight Nafion resin on SiO$_2$ made according to Illustrative Embodiment I, at a temperature of 100° C. and a LHSV (linear hourly space velocity) of 1 hour$^{-1}$. The effluent is fractionally distilled and yields 94% conversion of EO with a 94% selectivity to ethylene glycol (EG).

(b) The above experiment was repeated using the Rohm and Haas XN1010 H, a sulfonated polystyrene ion exchange resin, under the same conditions. The conversion of EO was 19% and the selectivity to EG was 67%.

(c) A thermal hydration of EO:H$_2$O solution in a weight ratio of 1:10 was carried out at 100° C., under 2 psi for 1 hour. The conversion of EO was 30% and the selectivity to EG was 85%.

This demonstrates the high conversion at high selectivity offered by the —(CF$_2$-SO$_3$H) ion exchange resins over conventional ion exchange resins and thermal hydrations.

ILLUSTRATIVE EMBODIMENT III

Polyethylene (4.0 g, USI microthene, m.p. 140° C., 38 micrometer particle size (400 mesh) was added to 165 g of perfluoro kerosene H (distilled after washing with sulfuric acid) in a UV irradiation apparatus. The mixture was vigorously stirred while passing in a mixture of oxygen of 1 liter/hour and sulfur dioxide at 5 liters/hour and irradiating with a mercury vapor lamp at 25° C. for 7 hours. The reactor tube around the light source was cleaned and irradiation with O$_2$/SO$_2$ flow continued for 6 hours. Once again the reactor tube around the light source was cleaned and irradiation with O$_2$SO/$_2$ flow continued for 7 more hours. The solids were collected by filtration and washed with perfluorohexane. After drying on the rotary evaporator for 2 hours at 25° C. and 1 mm, the product was washed with water until the wash water was colorless and neutral. The product was dried in a vacuum oven at 50° C. and 1 mm for 72 hours. The dried powder weighed 3.3 g. Titration with 0.1 N sodium hydroxide showed the presence of 1.0 meqiv/g of sulfonic acid. Analysis by neutron activation showed 3.4% sulfur.

Perfluorination of Polyethylene Sulfonic Acid

The fluorine (Matheson ¼ lb cyclinder at 300 psi reduced to 20 psi) was passed through a U-shaped copper tube packed with sodium fluoride to remove small amounts of hydrogen fluoride and then through a precalibrated glass/SS rotometer containing an aluminum float. The fluorine was then diluted with nitrogen and passed into three 100 ml teflon reactors in series. Copper tubing and teflon tubing was used throughout the system. The first teflon reactor was empty in case the reaction mixture sucked back. The second teflon reactor was charged with 1.1 g of polyethylene sulfonic acid, 3.0 g of sodium fluoride and 130 g of distilled perfluorokerosene 195 (PCR). Teflon tubing extended down into the liquid phase for bubbling and mixing. The contents of the second reactor were stirred with a teflon stirring bar. The third reactor was packed with 100 g of 8-14 mesh soda lime to remove any unreacted fluorine or hydrogen fluoride. A blow-out bubbler containing 4 inches of perfluoroalkane 195 was attached to the system. To the blow-out bubbler was attached a tube containing 200 g of 8-14 mesh soda lime. Finally, attached to the third reactor was bubbling device containing 0.5 M potassium iodide solution to insure that no fluorine was exiting from the soda lime. The initial fluorine flow rate was 2.5 ml/min diluted with a 10 ml/min of nitrogen which was continued for 8 hours. Fluorine flow was turned off each evening and the system swept out with nitrogen at 30 ml/min for 16 hours. Solids were collected by filtration and washed with perfluorohexane. The product was then dried in the vacuum oven at 25° C. and 1 mm for 2 hours to remove the perfluorohexane. The product was then washed with $10 \times 100$ ml portions of water to remove NaF and Na-F·HF. The last several washings were neutral. The dried product weighed 3.1 g and was cream colored. Analysis showed 72.8% fluorine, 25.0% carbon, 0.7% sulfur, and 0.15% hydrogen. Titration with 0.1 N sodium hydroxide showed the presence of 0.21 mequiv/g of sulfonic acid (70% of theory).

The procedure described above may be used to make the fluoroalkyl sulfonic acid ion exchange resins of formulas 2-4.

ILLUSTRATIVE EMBODIMENT IV

A supported resin of formulas 2-4 according to Illustrative Embodiment I and III is ground into particles having a surface area of greater than 100 m$^2$/g and placed in a flask. A water/ethylene oxide solution is brought into contact with the resin and the resulting products are separated by distillation. Ethylene glycol is obtained.

ILLUSTRATIVE EMBODIMENT V (a) A solution having a water to ethylene oxide weight ratio of 10:1 was passed over a bed of 2 g of Nafion (6% wt) on silica made according to Illustrative Embodiment I at a temperature of about 92° C. and an LHSV of 0.025 hour$^{-1.}$ Product analysis showed a 56% conversion of EO with a 94% selectivity to EG.

(b) Example (a) above was repeated using a polystyrene sulfonic acid resin known commercially as Amberlite IR-120. (Rohm and Haas) in place of the Nafion/silica catalyst. Product analysis showed a 10.1% conversion of EO with a 94% selectivity to EG.

(c) Example (a) above was repeated using Nafion/silica at 115° C. Product analysis showed a 74% conversion of ethylene oxide with a 94% selectivity to EG.

(d) Example (c) above was repeated using Ir-120 H as the catalyst. Product analysis showed a 72% conversion of EO with a 92% selectivity to EO.

(e) Example (c) above was repeated using Rohm and Haas XN1010H sulfonated polystyrene resin. Product analysis showed a 80.5% conversion of EO with an 89% selectivity to EG.

What is claimed is:

1. In the process of adding water to ethylene oxide to produce ethylene glycol by contacting ethylene oxide with water in the presence of an acid ion exchange resin at an initial water to ethylene oxide weight ratio varying from about 1:1 to about 100:1 and a temperature between about 50° C. to about 110° C., the improvement which comprises using as the acid ion exchange resin a resin selected from the group consisting of resins having the formulas:

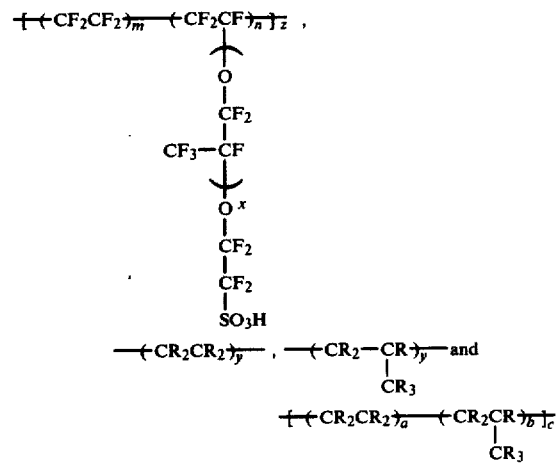

where n, m, x and z are integers such that the equivalent weight is less than 2000 and where R is individually a hydrogen, a fluorine and a —SO$_3$H group, at least some of the carbons attached to greater than one R have both a fluorine and a —SO$_3$H group attached thereto and where a, b, and c are integers the sum of which are such that the equivalent weight is less than 2000.

2. The process of claim 1 wherein the resin is deposited on a support selected from the group consisting of silicon dioxide, alumina, clay and porous glass beads.

3. The process of claim 2 wherein the initial weight ratio of water to ethylene oxide ranges from about 3:1 to about 15:1.

4. In the process of adding water to ethylene oxide to produce ethylene glycol by contacting ethylene oxide with water in the presence of an acid ion exchange resin, the improvement which comprises using an acid ion exchange having the formula:

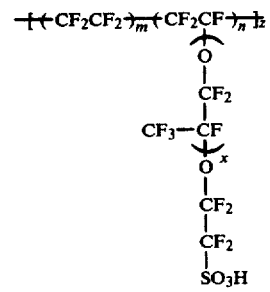

said resin being deposited on a silicon dioxide support, at an initial water to ethylene oxide ratio varying from about 3:1 to about 15:1 and a temperature of between about 50° C. and 110° C.

* * * * *